United States Patent [19]

Guruswamy et al.

[11] Patent Number: 5,004,583
[45] Date of Patent: Apr. 2, 1991

[54] UNIVERSAL SENSOR CARTRIDGE FOR USE WITH A UNIVERSAL ANALYZER FOR SENSING COMPONENTS IN A MULTICOMPONENT FLUID

[75] Inventors: Vinodhini Guruswamy; Donald A. Elliott, both of Bethesda, Md.

[73] Assignee: MedTest Systems, Inc., College Park, Md.

[21] Appl. No.: 229,503

[22] Filed: Aug. 8, 1988

Related U.S. Application Data

[63] Continuation-in-part of Ser. No. 8,554, Jan. 29, 1987, Pat. No. 4,762,594.

[51] Int. Cl.⁵ .................. G01N 21/27; G01N 21/63; G01N 27/333
[52] U.S. Cl. .................. 422/58; 204/153.1; 204/401; 204/409; 204/411; 250/227.14; 350/96.29; 350/96.3; 356/412; 422/82.03; 422/82.06; 422/82.11; 422/98; 436/150; 436/151
[58] Field of Search .............. 422/58, 68, 102, 98, 422/82.03, 82.06, 82.11; 204/1 T, 401, 409, 411, 153.1; 250/227, 227.14; 350/96.29, 96.3; 436/150, 151; 356/412

[56] References Cited

U.S. PATENT DOCUMENTS

| | | |
|---|---|---|
| Re. 31,879 | 5/1985 | Lübbers et al. ............ 422/68 X |
| 3,629,089 | 12/1971 | Luck . |
| 4,225,410 | 9/1980 | Pace . |
| 4,233,031 | 11/1980 | Matson et al. . |
| 4,397,725 | 8/1983 | Enzer et al. ............ 204/406 |
| 4,424,132 | 1/1984 | Iriguchi ............ 422/101 X |
| 4,549,951 | 10/1985 | Knudson et al. ............ 204/416 |
| 4,654,127 | 3/1987 | Baker et al. ............ 204/1 T |
| 4,762,594 | 8/1988 | Guruswamy ............ 204/416 X |
| 4,786,394 | 11/1988 | Enzer et al. ............ 422/81 X |
| 4,859,421 | 8/1989 | Apicella ............ 422/58 X |

Primary Examiner—Robert J. Warden
Assistant Examiner—Jill Johnston
Attorney, Agent, or Firm—Howard L. Rose

[57] ABSTRACT

The apparatus employs a method for accurate, reproducible analytical solution evaluation eliminating the need for a reference sensor by determining the activity of selected species employing species specific sensors and species combination sensors in conjunction with Nernst-type equations. The apparatus includes sensor structures for elimination of edge effects to signals thereby yielding accurate, reproducible measurements, and a cartridge structure adapted to incorporate an array of the new sensors for employment of the new method where the cartridge is particularly adapted for miniaturization, maintaining a fixed volume of solution for analysis and providing an anaerobic testing environment. Lastly, a compact instrument embodying miniaturization especially adapted for field use and use of the cartridge is provided herein.

16 Claims, 2 Drawing Sheets

UNIVERSAL SENSOR CARTRIDGE FOR USE WITH A UNIVERSAL ANALYZER FOR SENSING COMPONENTS IN A MULTICOMPONENT FLUID

RELATED APPLICATIONS

This application is a Continuation-in-Part of Ser. No. 008,554 filed Jan. 29, 1987 now U.S. Pat. No. 4,762,594.

TECHNICAL FIELD

This invention relates to the analytical measurement of solutions in sensor cartridges and the associated instrumentation that goes with it. A sensor cartridge contains an array of sensors and the required calibration fluids encapsulated and ready for discharge when measurements are being made. The sensor cartridge locks into the analyzer such that electrical connections between the two are made. When a sample fluid is introduced into the sensor cartridge in the analyzer the microcomputer controlled instrument makes the requisite measurements and then computes the concentrations that the sensors in the sensor cartridge are designed to measure.

BACKGROUND OF THE INVENTION

Traditional wet chemistry techniques in analytical chemistry and its use in the area of clinical chemistry have in the recent decades been improved. The improvements are based on the interaction of microprocessors with electromechanical devices that allow for these measurements to be made more precisely and easily.

In the subdiscipline of electrochemical measurements in the recent decade there has been considerable adaptation of the above methods to develop units that can self calibrate and measure the components in a sample. These units have been called cards or cartridges.

With the movement of chemistry tests outside the ambiance of a laboratory the need for these self contained test units for a wide variety of tests becomes important. Hence the need for a universal card or cartridge designed to be able to be modified at the factory to carry out a given range of tests which can work with one instrument becomes defined. At the factory the requisite range is fixed as according to customer requirements. Hence there will be cartridges that can carry out ionic profiles in soil or blood, and so on. To be able to carry out a wide range of tests it becomes important that the cartridge together with the instrument could lend themselves to a number of wet chemistry techniques ranging from electrochemical to optical methods.

The invention relates to a disposable universal sensor cartridge and an analyzer that can carry out a fixed range of tests that may use more than one method of analysis at the same time or different methods from time to time depending on the cartridge and the tests prescribed to it. Although the cartridge could work with a conventional reference electrode or source it specially lends itself for use with the comparator method developed by Guruswamy (patent application Ser. No. 07/008,554 to be U.S. Pat. No. 4,762,594 on Aug. 9, 1988) which does not require a reference electrode or source but rather a comparator electrode or source.

In clinical chemistry it is important for samples drawn from different parts of the body by devices ranging from "lancets" for finger pricks or finger sticks to acquire single drops of blood, to syringes for venous blood samples to be introduced easily into the cartridge with minimum contamination or evaporative loss from the sample. Our invention relates among other things to the drawing of blood from a punctured finger via a finger prick into the cartridge directly while allowing for other modes of introduction into the cartridge.

Most analytical systems are exposed to the ambient environment. They are not airtight. An airtight environment is desirable, first, to more closely match in-vivo conditions. Furthermore, it is important, for example, in blood gas analysis to avoid sample contamination from air so as to cause skewing of the results. This is particularly true in the analysis of blood gases but may pertain to measurement of other components as well. Lastly, to obtain a series of substance or component measurements from a sample, requires considerable time and many individual measurements. Not only is the time factor detrimental but, also, specimen contamination and chemical changes in the specimen are likely to occur. Hence, it is desirable to maintain an airtight measuring environment to achieve accurate measurements of certain substances, and most notably, blood gas concentrations. Lastly, most known systems do not contemplate fixing or providing fixed volume delivery. Elaborate stirring or mixing arrangements are used to insure uniform transport to the sensor. It would be desirable to conduct measurements of a fixed volume of solution and especially desirable to provide analysis requiring only a small volume of solution uniformly delivered to the sensor to make the measurements.

Other practical considerations arise relative to laboratory use by the clinician. In the event that a system is intended to be reusable, it is incumbent upon the operator or technician to insure that the electrodes are not contaminated when preparing for a test. Thorough cleaning and recalibration is necessary for each use. Such efforts require considerable labor and render cost ineffective the use of reusable systems especially in hospital laboratories or make inefficient their use in the field. Where disposable systems are employed, problems arise relating to the technician's reproducibility of the technique used.

Another aspect of electrochemical apparatus design and operation that has escaped attention in developments to date is the attribute of a compact, simply employable, field or laboratory use instrument which can be operated by persons having a minimum of skilled training. Miniaturized and standardized equipments are not available for providing analytical electrochemical measurements like those described above.

SUMMARY OF THE INVENTION

It is, therefore, an object of this invention to overcome the problems experienced with the use of prior art techniques and methods.

Still another object of this invention is to provide an apparatus for electrochemical measurement requiring single point calibration for potentiometric, potentiostatic or resistivity analysis.

Still another object of this invention is to provide apparatus for electrochemical substance concentration determinations with a minimum cost and a minimum of effort by eliminating the requirement for a reference electrode.

Yet another object of this invention is to provide apparatus for speedy measurements to avoid timedependent internal changes, to maximize stability and to minimize potential contamination of the sensors.

It is another object of this invention to provide apparatus minimizing potential technician error and avoiding the need for technician interpretation.

Still another object of this invention is to provide apparatus for solution analysis which maintains the solution in an airtight environment.

Another object of this invention is to provide a fixed volume of solutions for measurement although the volume introduced into the cartridge is not fixed.

Another object is for blood from a punctured finger be directly drawn into the cartridge.

Another object is to allow for the introduction of blood and other biological solutions to be introduced into the chamber easily.

Still another object of this invention is to provide measuring methods and apparatus equally applicable to a range of analytical purposes such as electrochemical and optical measurements.

Yet another object of this invention is to provide apparatus capable of miniaturization and which is capable of employing an array of sensors for real-time, multispecies solution analysis.

Another object of this invention is to provide a cartridge which is disposable or capable of reuse.

A further object of this invention is to provide a modular cartridge system where different cartridges for different measurements may be sequentially introduced to signal processing apparatus.

It is another object of this invention to provide a universal sensor cartridge capable of incorporating a number of different sensors for a broad range of different analytical techniques.

It is still another object that these cartridges are economical such that they could be disposed of after use.

Still other objects of this invention are satisfied by a cartridge for facilitating analytical measurement of a solution, comprising a housing and a chamber for containing a method of containing a predefined volume of solution whatever the solution added, the chamber having a first end and a second end and being disposed within the housing. Combined with the chamber are an inlet port in fluid communication therewith which is located proximate to said first chamber end, and a waste reservoir of preselected volume. The design is such that the fluid in the reservoir is not in direct communication with the chamber. Within the chamber is a means for substantially preventing fluid back-flow from said reservoir to said chamber and a sensor element disposed in the housing and interfacing with the chamber at a preselected location between the first end and the back-flow minimizing means. Lastly, the cartridge has a means for conveying signals generated by the sensor through and out of the housing.

This cartridge is constructed for a miniaturized instrument but could be extended for handling large numbers of samples in a conveyer as presently used in hospitals for mass screenings. The cartridge maintains the test solution in an airtight environment, requires introduction of only a small amount of solution for test procedures, is adapted for incorporation of a number of different sensors and sensor types and even contemplates disposability.

Still further objects of this invention are satisfied by providing a sensor for evaluating a species in solution. The sensor embodies a conductive element capable of conducting signals having a first surface of particular cross-sectional dimensions coupled with species specific reactive means for reacting with a selected active species in solution. The reactive means is in intimate contact with the conductive element and capable of generating a signal corresponding to the active species in solution. The reactive means is sized to cover the first surface and extend a substantial distance beyond the perimeter of the first surface to minimize edge effects.

Still another objective is in the case of clinical testing to be able to introduce a blood sample directly from a punctured finger via placing the finger with the freshly formed adherent drop of blood directly onto a depression on the sensor cartridge thereby allowing the blood to flow directly through capillary action (resulting from decreased surface tension due to surface treatment of the walls of the chamber) directly into the chamber containing the sensors for measurement of the designated components present in the whole blood sample.

DETAILED DESCRIPTION OF THE ILLUSTRATED EMBODIMENTS

For organizational purposes, the illustrated embodiments will be described first by the new method in the context of electro-chemical analysis of specified substrates; secondly, by the sensor structure in the form of an electrode; thirdly, by a sensor assembly in the form of a miniaturized electrode containing cartridge; and lastly, a miniaturized microprocessor based and solar powered instrument for field or laboratory use.

At the outset, it should be noted that the illustrated embodiments contemplate precise structures and miniaturization which are not necessary for practice of certain aspects of the invention. For example, it is evident that laboratory equipment of considerable size can be constructed. Also, multiple purpose cartridges incorporating reference electrodes can be provided each which embodies certain concepts described herein. Accordingly, it is not intended that the invention be so limited to the specific recitation below.

THE METHOD

Figure 1:
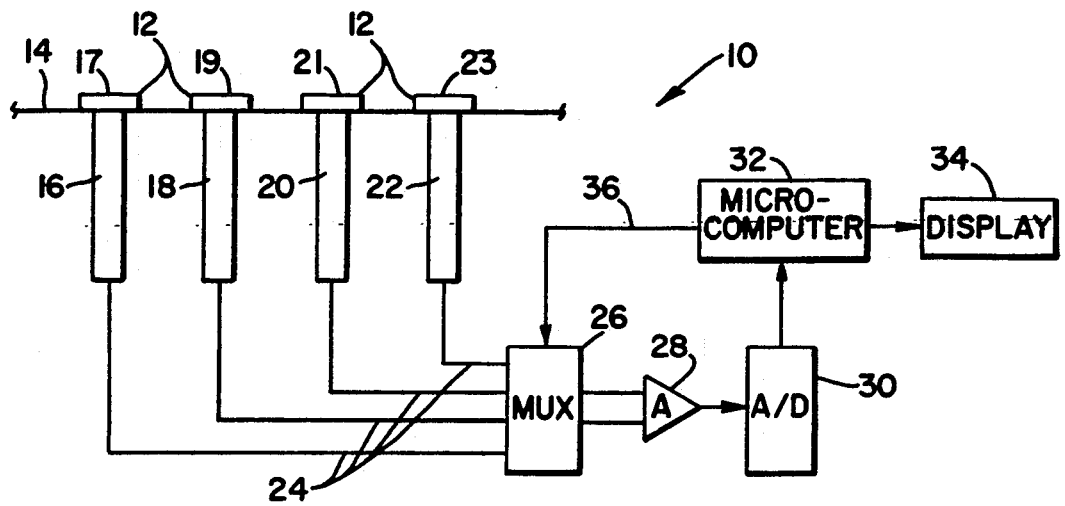
FIG. 1 is a schematic representation of a sensor arrangement of the invention.

Turning now to the method and referring to FIG. 1, it depicts multi-channel sensor system 10. Sensor 10 features an array of sensors 12 composed in this case of four individual electrode sensors, 16, 18, 20 and 22. For the purpose of illustrative simplicity, electro-active sensor 16 is deemed to be sensitive to a species A, sensor 18 is sensitive to a species B, sensor 20 is sensitive to species A and B, and sensor 22 is sensitive to species A and C. (These species may be chosen from many species such as potassium, sodium, chlorine, hydrogen ion, or selected biological and organic molecules.) All of species A, B and C are substances contained in a fluid which is to be electro-chemically evaluated using one of the two variations of the below-described method. More particularly, it is anticipated that a complex biological fluid such as blood will be subject to such an evaluation.

Although described in greater detail below, species specific covering membranes 17, 19, 21, and 23, corresponding respectively to sensors 16, 18, 20 and 22, are impregnated with ion selected materials where the electrodes are sensitive to A, B and C and combinations A and B as well as A and C, respectively. The membranes and sensors are so arranged to provide for a substantially uniform electrical signal caused by interaction between the target species in solution and the electroactive compound in the membrane. A corresponding charge develops between the membrane and the sensor thereby generating a charge distribution and potential proportional to the ionic activity of the species.

The principal variant of the inventive technique is now described with reference to potentiometric electrode sensors 16, 18 and 20. It should be appreciated by the skilled artisan that sensors 16, 18 and 20 represent half-cells where the combination of two half-cells provide an electro-motive force (EMF), representative of the potential difference between each of the respective sensors. Turning first to sensor 20, it is a combination electrode for species A and B, its electrical potential, in simplest form, is expressed by the equation $$E_{20half} = M_A \log C_A + M_B \log C_B + I_{AB} \qquad (2)$$

$M_A$ and $M_B$ are constants for species A and B, respectively, which for particular compositions and electrodes, can be predetermined and programmed into a calculation device. $C_A$ and $C_B$ are the concentrations of species A and species B, respectively. Equation 2 can be further reduced to the expression:

$$E_{20half} = M_{AB}[\log C_A + \log C_B] + I_{AB} \qquad (3)$$

where the quantity of the electroactive species impregnate into membrane 21 is carefully proportioned. For each such combination, before manufacture, it would first be necessary to evaluate the amounts to establish the most effective combination to obtain the simpler equation.

Moving now to the other electrodes, the electrical potential of sensor 18 which is sensitive to species B is expressible by the equation $$E_{18half} = M_B \log[C_B] + I_B \qquad (4)$$

Likewise, the half-cell potential of sensor 16 specific to species A is expressible as $$E_{16half} = M_A \log[C_A] + I_A \qquad (5)$$

To one of ordinary skill in the art, the foregoing equations represent the classical Nernst-type equations obtained from ion selective electrodes for measurement against standard electrodes. The instant invention, however, eliminates the need for a reference electrode and its contribution to the signal. The elimination of the reference electrodes is accomplished by establishing cells between sensors 16 and 20 and sensors 18 and 20, conveying the signals over wires 34 to multiplexer 26 which is commanded over wires 36 by microcomputer 32. The signals are sent to op-amp 28; in this case a differential amplifier, where signals from 16 and 18 are passed to analog/digital converter 30 and, ultimately, to microcomputer 32. The differential potentials corresponding to $E_{20} - E_{18}$ and $E_{20} - E_{16}$ are thus obtained. The differential signals are expressed by the equations $$E_{20-18} = (M_A \log[C_A] + M_B \log[C_B + I_{AB}) \\ - (M_B \log[C_B] + I_B) \qquad (6)$$

Put more simply $$E_{20-18} = M_A \log[C_A] + I_{AB} - I_B \qquad (7)$$

Correspondingly, $$E_{20-16} = M_B \log[C_B] + I_{AB} - I_A \qquad (8)$$

The slope values $M_A$, $M_B$, $M_{AB}$ and any other slope constants are known from prior testing of the particular electrode structures with standard solutions. These values are either inputted or stored in microcomputer 32 for inclusion into the equations. Therefore, with the slope values and the signal values known, the constants and the concentration values are determinable given measurement of a reference solution to determine the constants. In order to solve the equations, a reference solution having known concentrations of species A and B is measured. Since the constants $I_A$, $I_B$ and $I_{AB}$ are the same for both solutions, their contribution to the equation is subtracted out:

$$E_{20-18standard} - E_{20-18test} = M_A(\log[C_A]_{(standard)}) - M_A \log[C_A]_{(test)} \qquad (9)$$

Knowing the signal potential and the slope (M) values permits direct calculation of $C_A$ and $C_B$. By the foregoing, to obtain differential measurements of two distinct species requires only three electrodes; one electrode being selective for the combination of both species being tested and, then, two individual electrodes selected to each of the selected species being tested. Viewed simplistically, the combination electrode provides a signal corresponding to the activity of A+B where if the contribution of species A is substracted from the signal, the concentration of B is determined. Correspondingly, where the contribution of species B subtracted from the combinational electrode value, concentration of species A is determinable.

A second method for analysis of a greater number of species, can be practiced by the invention. Employing the foregoing principles, the concentration of a third species, C, may be determined by employing, at minimum, the fourth combination electrode 22 sensitive to species A and C. The concentration of C is determined by subtracting the signal produced by electrode 16 from electrode 22. In such a case the calibration solution must also include species C.

It should now be readily appreciated that the inventive method requires only one additional electrode to the number of species being evaluated. Mathematically, if N is the number of species targeted for analysis, only N+1 sensors are required to practice the technique. Moreover, the technique requires measurement of only two species containing solutions, the calibrant and the unknown solution.

A multiple combination system, as described above in the second embodiment, may exhibit some interference due to the presence of additional species (B) in solution. Accordingly, it may prove advantageous to have additional electrodes sensitive to species C alone or/and the combination of A, B and C. In such a case, the calculation apparatus are employed to provide comparative data between the species specific electrodes 16, 18 and 22 or the combination electrodes 20 and one sensitive to species A, B and C. Since multiple combination electrodes (more than two species) may be subject to electro-chemically synergistic interaction, anomalous signals may result. Hence, it is suggested that each electrode's sensitivity be limited to two species.

In summary, this invention permits evaluation of a solution for (N) separate species requiring only two measurements, the unknown solution and the calibrant solution, using only (N+1) electrodes.

Some aspects of the above-described technique should now be underscored. Principally, in the context of electro-chemical analysis, the method dispenses with the need for a reference electrode and, therefore, eliminates considerations for junction potential. Furthermore, elimination of the reference electrode minimizes "drift" problems by reducing the drift occurrence to two similarly structured electrodes. Rather than exhibiting relative combined drift of both the reference and species specific electrode each contributing its own district drift due to dissimilar geometries, compositions, etc., employing similarly structured and composed electrodes provides comparatively uniform drift. Hence, the drift component is often negligible or linear and assessable. It is not exponential and difficult to assess. (Drift is squared due to the separate contribution of reference and species electrodes.) Secondly, the method lends itself to use in miniaturized devices.

It should be evident to the skilled artisan that not only does the instant method provide a labor saving technique for multicomponent electro-chemical analysis but also is an expedient for rendering real-time results when needed. These benefits are especially important in a clinical chemical environment during sensitive procedures such as surgery on a human patient.

ELECTRODE STRUCTURE

Conventional electrodes may be used with foregoing techniques and in the below-described apparatus. For example, wire, wire coated, and film electrodes, thick or thin film electrodes of a redox, semiconductor or type involving a polymeric matrix immobilizing an electro-chemically active receptor impregnated therein, can be used. More specifically, variants of the thin film electrode described in U.S. Pat. No. 4,214,968, the graphite electrode described in U.S. Pat. No. 4,431,508 and the convex-domed electrode described in U.S. Pat. No. 4,549,951, may all be employed in the arrangements and methods described herein and for that reason are incorporated by reference.

The modification of the foregoing electrodes involves the selection of the ion selective electrode region or membrane having a substantially greater cross-sectional area than the underlying conductor in order to promote uniform charge density between the solution and the conductor.

It has been suggested previously (see U.S. Pat. No. 4,549,951) that a convex geometric configuration of the membrane contributed to promote uniformity of signals from transport of the electroactive species of an ion selective membrane to the interfacing cross-section of the conductor and, thus, accuracy and reproducibility of measurements. The dome-shaped membrane electrode was conceived of for this purpose. However, what went unrecognized is the contribution of edge effects to space charge distribution and transport phenomena and, hence, (adherence from surface tension, greater electron transfer, etc., generated along the perimeter of the conductive body) to the signal. Basically, edge effects result from nonuniform layers of charge distribution between the interfaces of solution, the membrane and the electrically conductive member of the electrode. The nonuniformity is particularly pronounced along the perimeter of the conductor and membrane due to surface phenomena and exposure to a relatively greater volume of solution with a corresponding higher density of flux. This factor gives rise to slope variations from electrode to electrode even for the same species.

It has now been found that the elimination of edge effects promotes signal uniformity without a need to restrict the configuration of the membrane to a particular geometry. Accordingly, it is now believed to be no need for the membrane to possess any particular geometric configuration (dome shape, etc.) but rather to provide an area of sufficiently greater size than the conductor cross-section to minimize edge effects. Indeed, it is preferred to provide a membrane surface area having at least approximately twice the size of the cross-sectional area of the conductor. However, more precisely, the degree of membrane overlap is mathematically accessible from the membrane/electrode geometry and classical electron transport equations.

Figure 2:
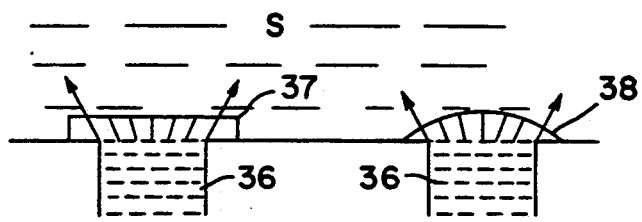
FIG. 2 is a graphical depiction of flux density distribution across sensors.

Referring briefly to FIG. 2, it graphically depicts the electron pathways between solution S, rectangularly cross-section membrane 37, and domed membrane 38 to underlying conductors 36. Although some signal contribution occurs from the outer membrane regions, the predominate uniform flux distribution is generated from the region overlying the electrode and a bevelled region of between 30° to 45° flaring from the edge of conductor 36. To promote uniformity of edge effect and, therefore, avoid nonuniform measurement, the membrane area is increased to extend well beyond the perimeter of the conductor.

Figure 7:
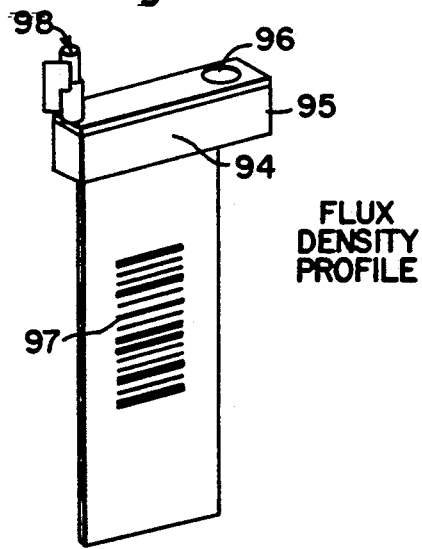
FIG. 7 is a perspective view of a disposable, sensor-containing cartridge.
Figure 8:
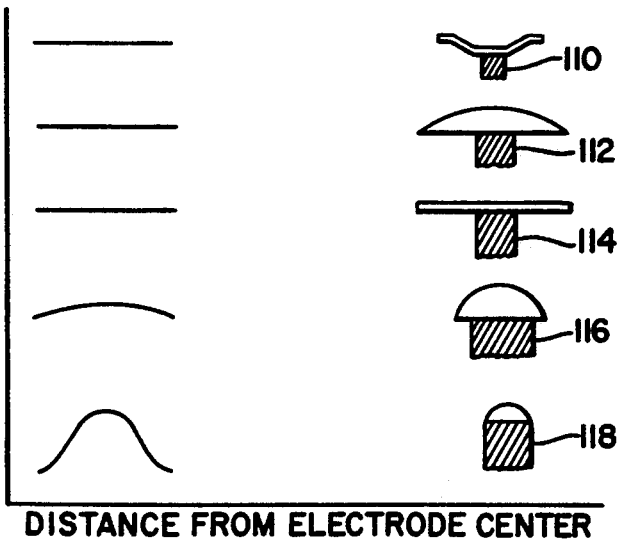
FIG. 8 is a graphical representation of the sensor construction and flux density variations caused by edge effects.

Turning briefly to FIG. 8, it represents the contribution of edge effects to various electrode structures. Electrodes 110, 112 and 114, having concave, convex and flat membranes, respectively, each demonstrate uniform flux density across the entire conductor surface. Convex domed electrode 116, having a membrane extending a little beyond the conductor perimeter, exhibits a small deviation in flux density. Electrode 118, with no extension exhibits considerable flux density variation across the conductor surface. As stated above, FIG. 7 underscores the fact that this invention contemplates the miniaturization of nonuniform flux density along the edge of the electrode by providing a membrane of considerably greater cross-section than the underlying conductor surface. Hence, the instant invention contemplates that the electrode will contain a species reactive region or membrane having an overlap so as to possess a solution interface area considerably greater (approximately twice) than the cross-section of the conductor.

In summary, the electrodes contemplated for use in the instant invention are known electrodes modified to provide an increased electro-chemically active surface of considerably greater surface contact area than the underlying electrically conductive region of the electrode to eliminate edge effects and corresponding uneven flux density.

THE CARTRIDGE

The contemplated sensor containing cartridge is intended to contain several microsensors of similar or different types, maintain an airtight sample chamber, and a container for a calibration fluid or sample that can be released into the chamber for measurement. A reservoir for waste fluids after measurement is also provided so that the next fluid can be introduced into the sample chamber by displacement, provide a fixed volume in the sensor chamber, for the direct introduction of the blood into the cartridge from a finger prick. Easy operation without a technician and for signals coming from the microsensors whether they be optical, electrochemical or otherwise that they be processed to give the concentration or activity of the species.

Figure 3:
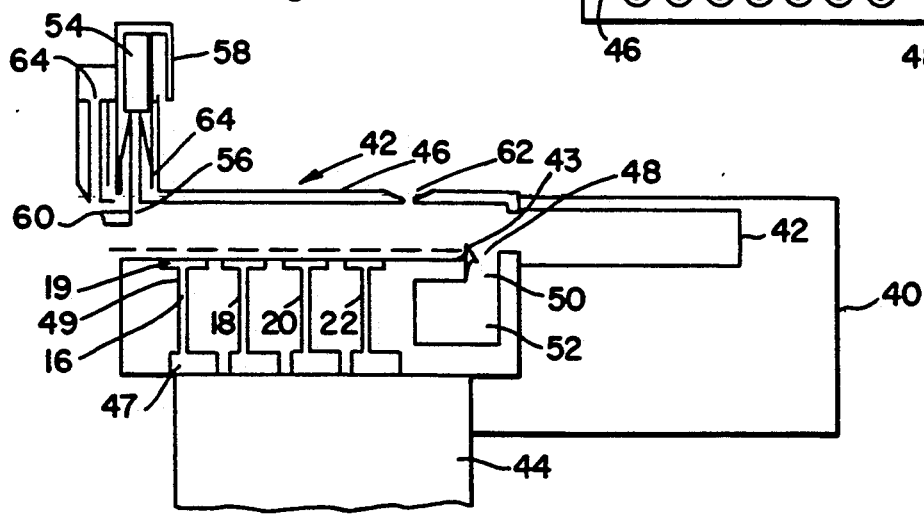
FIG. 3 is a perspective view of a sensor cartridge of the invention.

Referring now to FIG. 3, it depicts cartridge 40 comprising two principal sections, chamber housing 42 and lower insert region 44. Contained within chamber housing 42 is fixed volume chamber 46 designed, typically, to hold a volume of less than one milliliter and preferably between 10-50 microliters. Chamber 46 is generally of a rectangular configuration and is sealed within chamber housing 42. Within chamber housing 42, sensors 16, 18, 20 and 22 are embedded and disposed in an array on the lower surface of chamber 46. The sensors are electrically isolated from each other and are positioned in chamber 46 in a manner where fluid introduced therein will completely cover sensors 17, 19, etc. which may or may not have a coating on them to bring about specificasity or reactivity.

Disposed transversely along one side of chamber 46, is vented waste reservoir 50 having a volume capacity of 10-50 times that of chamber 46. One direction flow vents 52 are provided at selected locations in order for air or gas to escape and allow fluid from chamber 42 to evenly flow into reservoir 50. Between reservoir 50 and the sensors are located furrow 48 and weir 43. Furrow 48 and weir 43 are designed to keep the volume of the chamber fixed such that any excess fluid flows into the reservoir. Physical separation between the fluid being measured and the waste fluid in the reservoir 50 prevents interfacial mass transfer between the waste fluid and the calibration fluid. It is noted that the weir may be unnecessary where the cartridge is of a design to take advantage of surface tension to stabilize the sample fluid, on the one hand, and the calibrant fluid, on the other hand, over the sensor.

At the opposite end of chamber housing 42 from waste reservoir 50 are calibration fluid input port 56, calibration fluid syringe 54 and specimen inlet port 62 with specimen input element 60 extending therefrom. Specimen input element 60 could provide a rubber septum across its upper surface for injection of the specimen into element 60 into chamber 46 from a conventional syringe or, alternatively, a capillary tube. Alternatively a capillary hole that can be presented to a finger that has been pricked to allow for blood to flow into the chamber in the analysis of whole blood that operate on blood from a finger stick. Or alternately from the finger directly to the capillary tube. It is desirable to inject or introduce an amount of specimen fluid slightly more than the volume of the chamber 46, any excess will flow into furrow 48 and, subsequently, into waste reservoir 50.

Calibration fluid syringe or capsule 54 contains an approximate excess volume to that required in the calibration chamber of an appropriate calibration fluid containing substances for which the sensors arrayed within chamber 46 are sensitive. This approximate volume of calibration fluid is injected into chamber 46 by turning and depressing plunger 58 where the fluid flows through input port 56 and into the chamber. This plunging action can displace and wash away any fluids already present in the chamber.

Moving now to the structure of lower insert region 44, like chamber housing 42, it is preferably composed of a suitably rigid, strong, polymer having the conductive elements (graphite, conducting wire, optical fibers, etc.) from sensors 16, 18, etc., extending through its length.

By providing significant sensor elongation, especially when electrochemical measurements are performed, the elongation minimizes signal interferences from adjacent sensors. As a practical matter, during manufacture of a membrane covered electrode, the membrane is deposited over the conductor in a partially gelled condition. The remaining solvent, generally organic, is then evaporated. However, some solvent will migrate into pores in the cartridge body. Migrating solvent can carry with it the electroactive species. Hence, the cartridge body, itself, may be sensitized or even cross-sensitized. Where electrodes are positioned very close to each other, cross-contamination can occur. Thus, a species specific electrode may generate a small signal corresponding to another species for which the neighboring electrode is sensitive. This possibility is enhanced when the cartridge body is very short, the degree of migration is correspondingly reduced, and intermingling occurs close to the sensor receptor surface. By elongating the sensors body in the cartridge, gravity causes the solution bearing, residual electroactive species to follow a downward path adjacent the electrode instead of transverse intermingling a short distance from the receptor membrane. Hence, it is preferred that the cartridge be of sufficient length to minimize such effects. In the case of thin film applications the design lends itself to masking and allows for a large number of these units to be handled at the same time.

Returning to the structure of cartridge 40, waste reservoir 50 extends toward the bottom of lower insert region 44. Projecting from the bottom of chamber 44 are electrical contacts 47 which provide electrical communication between sensors 16, 18, and an appropriate signal detector Due to potential internal signal interference or interference from external electrical noise, it may be desirable to insulate each of sensors 16, 18, etc. Accordingly, sensor 16 is illustrated with insulative sheathing 49 disposed therearound. If all the sensors are so insulated, the opportunity for electrical signal interference is minimized.

In brief, cartridge 40 is used by introducing sufficient volume of the specimen fluid into chamber 46 via inlet port 62 to fill chamber 46. This introduction can be done by a number of different ways such as using a syringe, or a capillary tube or by direct introduction from the finger to the port where the fluid is drawn into the chamber by capillary action. Measurements of the electro-chemical activity are made via the array of sensors. Once measurements are taken, an excess volume in relation to that of the calibration chamber of calibration fluid is introduced via a plough 54 through input port 56 which washes the specimen fluid from chamber 46 into furrow 48 over weir 43 and into waste reservoir 50.

Figure 4:
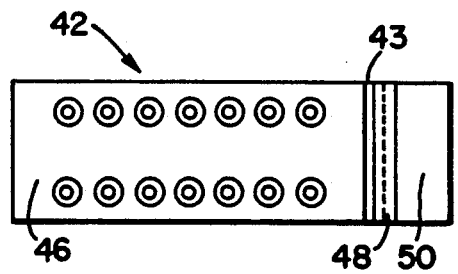
FIG. 4 is a top view of a sensor array.

In FIG. 4 is illustrated an alternative embodiment of cartridge chamber housing 42 and chamber 46. In this embodiment there is an array of fourteen sensors which have the capacity for analysis of as many as thirteen electrochemical active species. At one end of chamber 46, like the embodiment in FIG. 3, is disposed waste reservoir 50 for containing the analyzed specimen sample and the volume of calibration fluid employed for washing out the specimen fluid from chamber 46. Between reservoir 50 and the array of sensors is disposed furrow 48 and weir 43. Weir 43 in this case is positioned between the furrow and the sensors and assists to define a specific volume of fluid that will be contained within chamber 46. The fluid introduction may follow the steps described above or, alternatively, the calibrant may first be introduced into chamber 46 and measurements taken followed by introduction of the specimen solution into the chamber with measurements being taken of the specimen fluid. Where the calibrant is first introduced, it is possible to eliminate particular washing steps by providing a relatively substantial volume of specimen fluid to displace the calibrant solution, develop an equilibrium and be subject to measurement. Any excess specimen fluid will flow into waste reservoir 50.

The above-described cartridge embodiments are contemplated as being disposable as they would be composed of a relatively, inexpensive polymeric material. However, it is also possible to reuse the cartridge, given the inclusion of reusable sensors within the cartridge, by properly cleaning and otherwise freeing cartridge 40 from contamination. As would be expected in such an embodiment, reservoir 50 would be provided with an appropriate fluid outlet near or at the bottom of the reservoir in lower insert region 44 in order to permit a series of appropriate washings. Another alternative construction would be to provide an open-topped fluid containing chamber 46. This, in certain cases, would be undesirable as it would eliminate the airtight environment by exposing the species and calibrant to an ambient atmosphere. (As noted above, particularly in the context of biomedical measurements, it is preferred to maintain an airtight environment.) For this reason, it is suggested that chamber 46 and waste reservoir 50 be flushed with a neutral gas such as nitrogen following construction and prior to use to minimize the presence of atmospheric oxygen and carbon dioxide during testing.

An additional construction variant includes modifying element 60 to be a flow diversion valve or dispenser adapted to extract a sample directly from the source. For example, element 60 may be combined with a catheter to extract blood directly from a patient's body. Point contacts 47 may also be modified both in structure and position. They may exit lower region 44 on its side and be of a structure to establish wiping electrical contact with an appropriate mating receptacle.

Lastly, it is possible to modify the cartridge for instruments other than electrochemical analyzers. For example, optical fibers could be incorporated for measurement of fluid optical properties. In this case, it would be suggested to have source fibers and receptor fibers disposed in an array to maximize optical transmission and reception. Preferably, conventional available coaxial fibers would be used. Moreover, the upper surface of chamber 46 can be coated with an optically reflective material. An additional variant would be optical colorometric analysis of the covering membrane impregnated with a species specific interactive substance which undergoes a color change upon reaction. Color changes can be detected using coaxial optical sensors. As one further variant, optical and electrochemical sensors can be combined in the same cartridge.

In summary, cartridge 40 serves the function of positionally stabilizing and maintaining a specific geometry between the sensors housed therein, defines a precise volume of fluid for analysis, provides an airtight testing environment, avoids sensor contamination, provides waste contaminant while avoiding fluid intermingling and means for precise alignment of the sensors with appropriate detection apparatus. Moreover, it is adaptable for use with a host of conventional sensors, for example, potentiometric, potentiostatic, resistance, colorometric, etc., analysis.

THE MINIATURIZED ANALYZER

Figure 5:
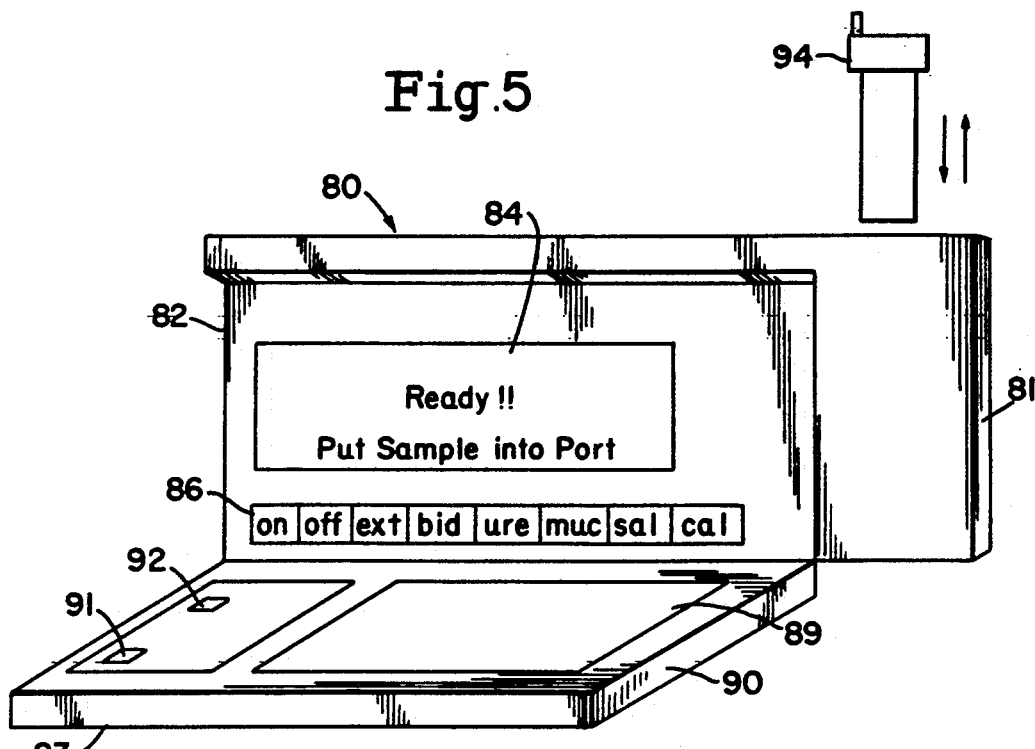
FIG. 5 is a perspective view of a compact instrument of the invention.
Figure 6:
FIG. 6 is a view of the instrument in a folded configuration.

In FIGS. 5 and 6 are depicted a miniaturized instrument for use of a sensor containing cartridge, like that described above, containing electrodes, like those disclosed above, and contemplating measurements by the analytical techniques set forth above. Compact instrument 80 dedicated for biomedical use, is comprised of fold-up case 82 featuring upper region 81 and fold-out region 83 which are hinged (not shown). The electronic components employed within the case are commercially available. They are microprocessors, random access memories (RAM)s, read only memories (ROM)s, amplifiers, switches, analog to digital converters, power capacitors, transformers, etc.

The principal features of upper region 81 are liquid crystal display panel 84, controlled by the microprocessor (not shown) and a row of actuation buttons 86 for activating the particular function desired. Upper region 81 is also provided with an appropriately sized cartridge receptacle (not illustrated) to permit insertion of sensor cartridge 94 therein. Once inserted, as described above, the electrodes contained by cartridge 94 are processed and are displayed on the liquid crystal screen. Buttons 86 facilitate selection of the desired, W for example, particular blood gas concentrations or even blood pressure, on display 84. The receptacle can be modified to include an optical character recognition device or magnetic pickup device for reading information placed on the side of cartridge 94. For example, a bar code or piece of magnetically encoded tape can be positioned on the cartridge which would automatically input data such as slope values (see method above), identify specific sensors and combination sensors, etc. The modification would eliminate the need for the operator to input such values and information by, for example, a programming keyboard (not illustrated). Furthermore, the codes could reprogram buttons 86 for specific tests performed by specific cartridges.

Lower panel 83 features a solar panel 89, RS232 port 90 and plug-in adaptors 91 and 92 for connecting peripherals equipment such as a phonocardiogram and blood pressure monitor. Signals from a phonocardiogram or blood pressure monitor are displayed on the LCD following appropriate signal processing by the microprocessor and activation by the appropriate button. RS232 port 90 permits digital communication between the unit and a remote digitalized patient information storage area should it be desirable to convey the data processed from cartridge 94 or from ancillary equipment such as the above-stated phonocardiogram or blood pressure monitor to a computer, etc. Due to the advances in microprocessor and electronics technology, in addition to the miniaturization provided by the structures and techniques defined above, it is possible to provide a physical embodiment of instrument 80 adapted to fit into a pocket. As such the dimensions should not be in excess of 3¼ inches wide, 9 inches long, and 1¼ inches deep. Furthermore, the weight of the entire unit can be restricted to approximately one-half pound. Hence, the unit is easily handled and stored. Indeed, it is possible for a doctor to slip the entire unit, when folded, as depicted in FIG. 6, into his coat pocket following patient examination. Moreover, given the provision of solar panel 89 for generation of needed power, it is not necessary for the physician, medical technician or clinician to have an electrical power outlet readily available. Alternatively, chemical batteries, etc., can be incorporated as an appropriate power source. Thus, the unit is readily adapted to use in the field, as for example, at accident scenes, etc. The RAMs incorporated in instrument 80 permit the medical technician or doctor to make a series of patient samplings which can be later recalled and inputted into a primary patient data bank.

Now turning to FIG 7, a portable, disposable variant of cartridge 40, described above and contemplated for use with unit 80, is illustrated. Primarily, cartridge 94 includes upper region 95 and lower region 97 where lower region 97 is adapted to be inserted into the complementary aperture provided in unit 80 and establish electrical contact therebetween. It is contemplated that appropriate electronic circuitry and control like described in reference to FIG. 1 is incorporated into instrument 80 to provide fluid analysis by the method described. The ROMs employed in such a unit, for example, would hold slope information for particular substances relative to the particular electrode structure.

Moving now to the particular configuration of upper region 95, it includes a chamber containing calibrant solution and push-button calibrant injector 98 for flooding the specimen chamber (not illustrated). Further illustrated is specimen port 96 for injection of blood or other appropriate fluid into the specimen chamber. In this embodiment, it is contemplated that the waste reservoir be contained entirely within upper region 95. The operation of this cartridge is identical to the procedures described earlier in this application.

As is readily apparent, pocket-sized unit 80 and cartridge 94 are directed to use by medical personnel, either in a hospital environment or in the field. Of course, the same principles may be employed in alternative disciplines such as environmental aquatic analysis.

Given the foregoing description of the system, the cartridge, the modified electrode structure and the single calibration referenceless technique, a host of modifications and variations thereto should now be apparent to one of ordinary skill in the art. It is intended that such modifications and variations fall within the scope of the invention as described by the appended claims.

We claim:

1. A re-useable cartridge for facilitating analytical measurement of a solution, comprising:
   (a) a housing,
   (b) a chamber having a cross-section for containing a predefined volume of solution, said chamber having a first end and a second end being disposed within said housing,
   (c) an inlet port in fluid communication with said chamber, said port being located proximate to said first chamber end,
   (d) a waste reservoir of preselected volume in fluid communication with said chamber and located proximate to said second chamber end,
   (e) inlet ports for introducing fluids directly into said chamber,
   (f) means for positively forcing fluid in said chamber to flow out of said chamber and into said reservoir,
   (g) means for substantially preventing fluid back-flow from said reservoir to said chamber,
   (h) sensor elements having cross-sections disposed in said housing and interfacing with said chamber at a preselected location between said first end and said fluid backflow preventing means; and
   (i) means for conveying signals generated by said sensor elements through and out of said housing.

2. The cartridge according to claim 1, further comprising means to enhance signal uniformity across the entire sensor cross-section.

3. The cartridge according to claim 2 where said sensor elements are ion selective electrodes, each of said electrodes, including a thin film membrane over an area of the electrode interfacing with said chamber which creates a membrane edge such that said membrane extends beyond the edge of the electrode to provide at least approximately twice the cross-sectional area of the electrode interface with said chamber.

4. The cartridge according to claim 1 where said sensor elements are of uniform geometric configuration at the interface of said electrodes with the chamber.

5. The cartridge according to claim 1 where the sensor elements are ion selective electrodes and said housing defines an upper region and a lower region,
   said chamber being contained within the upper region and further comprising a signal processing means for processing signals received from said sensor elements and connecting means to connect said sensor elements to said signal processing means.

6. The cartridge according to claim 5 wherein
   each of said electrodes includes a sheath of electrically insulated material such that cross-contamination of neighboring electrodes is minimized.

7. The cartridge according to claim 1 where said chamber has a bottom surface, and
   said sensor elements interface with said chamber along said bottom surface and said sensors extending through said housing.

8. The cartridge according to claim 1 where said reservoir is contained within said housing and has a volume of at least twice the chamber volume.

9. The cartridge according to claim 8 wherein said means for substantially preventing back-flow is a weir disposed between said sensor elements and said reservoir and extending across the entire chamber cross-section.

10. The cartridge according to claim 8 wherein said means for substantially preventing back-flow is a groove and a weir parallel thereto extending across said chamber between said sensor elements and said reservoir.

11. A cartridge according to claim 1 further comprising
    a second fluid inlet positioned proximate to said first end of said chamber and means for introducing a predetermined volume of calibration fluid through said second inlet and into said chamber.

12. The cartridge according to claim 11 further including
means for introducing a precise volume of the solution and calibration fluid into said chamber at substantially uniform pressure.

13. A cartridge according to claim 1 wherein
said sensor elements are optical fibers and further including means for conveying light to and from said chamber.

14. A re-useable, miniaturized cartridge for use in measuring at least two substances in solution adapted for insertion into a receptacle of predetermined dimension, comprising:
a housing having upper and lower regions, said upper region having a chamber of predefined volume;
a first inlet means for introducing the solution into said chamber,
a second inlet means for introducing a calibration fluid into said housing;
three substance sensitive means, two of said three substance sensitive means sensitive to one each of the substances and one of said three substance sensitive means sensitive to both of said at least two substances, each of the substance sensitive means being secured within said housing and having means for interfacing with said chamber and extending to the lower region of said housing;
a reservoir for receiving fluid displaced from said chamber, said reservoir being contained within said housing and extending into the lower housing region,
said reservoir having a fluid containing volume considerably greater than that of the chamber;
a fluid flow impedance means being disposed between said sensitive means and said reservoir;
wherein said lower housing region is adapted to be received within a complementary receptacle and said sensitive means establish signal contact with corresponding signal conductive elements within the receptacle.

15. The cartridge according to claim 14 where N equals the number of species to be measured such that $N+1$ sensitive means are needed for evaluation of said N species and said sensitive means are arrayed in said housing and said sensitive means are electrodes and the electrodes establish electrical contact with said receptacle.

16. The cartridge according to claim 14 where said sensitive means are electrodes having substance interactive elements and conductors such that the conductors have a periphery wherein the elements extend beyond the periphery of the conductors to minimize edge effects.

* * * * *